US008796493B2

(12) United States Patent
Merkel et al.

(10) Patent No.: US 8,796,493 B2
(45) Date of Patent: Aug. 5, 2014

(54) METHODS TO SEPARATE HALOGENTATED OLEFINS FROM 2-CHLORO-1,1,1,2-TETRAFLUOROPROPANE USING A SOLID ADSORBENT

(75) Inventors: Daniel C. Merkel, West Seneca, NY (US); Konstantin A. Pokrovski, Orchard Park, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 167 days.

(21) Appl. No.: 13/249,342

(22) Filed: Sep. 30, 2011

(65) Prior Publication Data

US 2013/0085308 A1  Apr. 4, 2013

(51) Int. Cl.
C07C 17/38 (2006.01)

(52) U.S. Cl.
USPC .......................................... 570/179; 570/177

(58) Field of Classification Search
None
See application file for complete search history.

(56) References Cited

U.S. PATENT DOCUMENTS

| 5,233,107 | A | * | 8/1993 | Jansen | 570/179 |
| 5,904,909 | A | * | 5/1999 | Yates et al. | 423/240 R |
| 7,803,283 | B2 | | 9/2010 | Pham et al. | |
| 8,252,964 | B2 | * | 8/2012 | Devic et al. | 570/177 |
| 2004/0030204 | A1 | | 2/2004 | Wilmet et al. | |
| 2007/0007488 | A1 | | 1/2007 | Singh et al. | |
| 2007/0197842 | A1 | | 8/2007 | Mukhopadhyay et al. | |
| 2009/0240090 | A1 | | 9/2009 | Merkel et al. | |
| 2010/0036179 | A1 | | 2/2010 | Merkel et al. | |
| 2011/0105809 | A1 | | 5/2011 | Devic et al. | |

FOREIGN PATENT DOCUMENTS

| JP | 04300842 A | * | 10/1992 |
| WO | 2004074225 A1 | | 9/2004 |

OTHER PUBLICATIONS

PCT ISR & Written Opinion issued in PCT/US2012/057193 dated Mar. 7, 2013.
Chatterjee, Abhijit, et al., Chlorofluorocarbons adsorption structures and energetic over faujasite type zeolites—a first principle study, Journal of Molecular Structure: THEOCHEM, Jul. 25, 2003, pp. 233-242, vol. 630, Issues 1-3.
Mariwala, Ravindra K., et al., Adsorption of halocarbons on a carbon molecular sieve, Microporous and Mesoporous Materials, Jun. 17, 1998, pp. 281-288, vol. 22, Issues 1-3.

* cited by examiner

*Primary Examiner* — Sudhakar Katakam
(74) *Attorney, Agent, or Firm* — Bruce O. Bradford

(57) ABSTRACT

The present invention provides a method for separating halocarbons. In particular, the invention provides a method for separating halogenated olefin impurities from 2-chloro-1,1,1,2-tetrafluoropropane (HCFC-244bb) using a solid adsorbent, particularly activated carbon. More particularly the invention pertains to a method for separating 2-chloro-3,3,3-trifluoro-propene (HCFO-1233xf) from HCFC-244bb, which are useful as intermediates in the production of 2,3,3,3-tetrafluoropropene (HFO-1234yf).

13 Claims, No Drawings

METHODS TO SEPARATE HALOGENTATED OLEFINS FROM 2-CHLORO-1,1,1,2-TETRAFLUOROPROPANE USING A SOLID ADSORBENT

FIELD OF THE INVENTION

The present invention provides a method for separating halocarbons. In particular, the invention provides a method for separating halogenated olefin impurities from 2-chloro-1,1,1,2-tetrafluoropropane (HCFC-244bb) using a solid adsorbent. More particularly the invention pertains to a method for separating 2-chloro-3,3,3-trifluoropropene (HCFO-1233xf) from HCFC-244bb, which are useful as intermediates in the production of 2,3,3,3-tetrafluoropropene (HFO-1234yf), using activated carbon as the adsorbent.

BACKGROUND OF THE INVENTION

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials associated therewith, it is desirable to use fluids having the lowest possible greenhouse warming potential in addition to zero ozone depletion potential. Thus there is considerable interest in developing environmentally friendlier materials for the applications mentioned above.

Tetrafluoropropenes, having zero ozone depletion and low global warming potential, have been identified as potentially filling this need. However, the toxicity, boiling point, and other physical properties in this class of chemicals vary greatly from isomer to isomer. One tetrafluoropropene having valuable properties is 2,3,3,3-tetrafluoropropene (HFO-1234yf). Thus, there is a need for new manufacturing processes for the production of tetrafluoropropenes and in particular 2,3,3,3-tetrafluoropropene.

U.S. Patent Pub. No. 2010-0036179 discloses a process to manufacture 2-chloro-1,1,1,2-tetrafluoropropane (HCFC-244bb) by reacting 2-chloro-3,3,3,-trifluoropropene (HCFO-1233xf) with hydrogen fluoride, in a liquid phase reaction in the presence of hydrogen chloride and a liquid phase fluorination catalyst. The hydrogen chloride is added into the reaction from an external source at a pressure of about 100 psig or more.

HCFC-244bb is an intermediate in the production of 2,3,3,3-tetrafluoropropene (HFO-1234yf) which is well known in the art as described in U.S. Patent Publication Nos. 2007-0007488 and 2007-0197842. HFO-1234yf has been disclosed to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid.

U.S. Patent Pub. No. 2009-0240090 discloses a process of making HFO-1234yf starting with chlorinated hydrocarbons. The process has three-steps. The first step involves fluorination of tetrachloropropene or pentachloropropane with HF to produce HCFO-1233xf. The second step involves hydrofluorination of HCFO-1233xf with HF to produce HFC-244bb. The conversion of HCFO-1233xf is not complete. Some of unreacted HCFO-1233xf is recycled back into the second step hydrofluorination reactor, but some of HCFO-1223xf is carried forward into the third step dehydro-chlorination reactor. The third and final step involves dehydrochlorination of HFC-244bb to produce HFO-1234yf product. Again, conversion of HCFC-244bb is not complete. Unreacted HCFO-244bb and HCFO-1233xf carried from the third step reactor is recycled back to the second step reactor. The presence of HCFO-1233xf in the third step reactor feed does not allow recycle of unreacted HCFC-244bb to the third step reactor. This results in larger size (lower capacity) of the second step reactor. Also, recycle of HCFC-244bb back into the second step hydrofluorination reactor may result in the formation of over fluorinated by-products such as 1,1,1,2,2-pentafluoropropane (HFC-245cb) and increased HF consumption.

It would be preferred to remove HCFO-1233xf and other halogenated olefins impurities produced in the first two process steps from the HCFC-244bb intermediate product prior to sending the feed into the dehydrochlorination reactor to produce final product HFO-1234yf. This would allow recycle of unreacted HCFC-244bb back to the third step reactor minimizing the yield loss.

HCFC-244bb and HCFO-1233xf are inseparable using conventional separation techniques known in the art since HCFC-244bb and HCFO-1233xf form a binary azeotrope or azeotrope-like composition which is described in U.S. Pat. No. 7,803,283. It has been found that HCFO-1233xf (and other halogenated olefin impurities) can be separated from HCFC-244bb using a solid adsorbent such as activated carbon or other solid adsorbents having similar properties.

When it is desired to separate halogenated olefin impurities including HCFO-1233xf from HCFC-244bb, the mixture of halogenated olefin impurities including HCFO-1233xf and HCFC-244bb can passed over solid adsorbent that preferentially adsorbs halogenated olefin impurities including HCFO-1233xf and then the two compounds can be separated. Essentially pure HCFC-244bb and HCFO-1233xf together with other halogenated olefin impurities can be recovered. Then essentially pure HCFC-244bb can be fed into the dehydrochlorination reactor where it is converted to HFO-1234yf. After separating unreacted HCFC-244bb from HFO-1234yf product, HCFC-244bb exiting dehydrochlorination reactor can be recycled back into the reactor to increase the yields of the final product HFO-1234yf.

SUMMARY OF THE INVENTION

The invention provides a method to separate halogenated olefin impurities from 2-chloro-1,1,1,2-tetrafluoropropane using a solid adsorbent that preferentially absorbs said halogenated olefin impurities including 2-chloro-3,3,3-trifluoropropene (HCFO-1233xf) using a suitable solid adsorbent, such as activated carbon.

Activated carbon is the preferred solid adsorbent used in this invention. In certain embodiments, the activated carbon is coconut shell based activated carbon. In certain embodiments, the activated carbon is coal based activated. In certain embodiments, the activated carbon is designed by the manufacturer for use in vapor phase applications. In certain embodiments, the activated carbon is designed by the manufacturer for use in liquid phase applications. Calgon Carbon Corporation of Pittsburgh, Pa. manufactures and sells a number of such activated carbons, including products having the following designations; BPL, RVG, OVC, COCO, AT-410, and VPR, to name but a few.

One measurement used to characterize activated carbons is the Iodine Number. The Iodine Number is generally used as a measure of activity level, a higher number indicates a higher degree of activation, and it also serves as an indicator of the micropore content of the activated carbon. The Iodine Number is defined as the milligrams of iodine adsorbed by one gram of carbon when the iodine concentration in the residual filtrate is 0.02 normal.

In the present invention, activated carbons having a minimum Iodine Number of 900 are expected to adsorb at least a portion of the olefin impurities. Activated carbons having a minimum Iodine Number of 1000 are expected to adsorb more of the olefin impurities. Activated carbons having a minimum Iodine Number of 1100 are expected to adsorb even more of the olefin impurities. Finally, activated carbons having a minimum Iodine Number of 1200 are expected to adsorb still more of the olefin impurities. Other solid adsorbents having properties similar to those of the activated carbons are also expected to be useful herein.

The invention further provides a method for removing halogenated olefin impurities from a mixture containing 2-chloro-1,1,1,2-tetrafluoropropane and halogenated olefin impurities by passing the mixture over the solid adsorbent or by adding a solid adsorbent to the mixture. Then collecting essentially pure HCFC-244bb and recovering absorbed halogenated olefin impurities by means known in the art. The preferred solid adsorbent is activated carbon.

The invention further provides a method of purifying the crude HCFC-244bb produced via fluorination of HCFC-1233xf, feeding purified HCFC-244bb into dehydrochlorination reactor to form HFO-1234yf product, and recycling at least a portion of unreacted HCFC-244bb, after separating it for HFO-1234yf product, back into dehydrochlorination reactor.

Adsorbents employed in this invention, especially the activated carbons, can be regenerated by heating the adsorbent to drive off the materials adsorbed. Use of a vacuum and/or an inert gas stream can further be employed for the regeneration of the adsorbent. If desired, the materials driven off of the adsorbent can be trapped, for example, in a dry-ice trap, for further purification and/or use.

It will be understood that the terms adsorbent, adsorbed or the like, as used here, are not limited to adsorption in the thermodynamic sense, although thermodynamically-controlled adsorption is included. It is intended that these terms encompass whatever processes or mechanism, or combinations thereof, are present herein, by which the halogenated olefin impurities including HCFO-1233xf are, in fact, removed from the mixture with HCFC-244bb.

DETAILED DESCRIPTION THE INVENTION

In a method of preparing a HCFC-244bb precursor, reagents are fluorinated with hydrogen fluoride. This may be done, for example, by the liquid phase or gas phase catalytic fluorination of $CF_3CCl=CH_2$ (HCFO-1233xf) with HF to yield HCFC-244bb. The reaction products of such precursors include HCFC-244bb, unreacted HCFO-1233xf, unreacted HF and small amounts of other halogenated olefins. Upon removal of the HF, a pure organic composition is formed and is then available for separation into its component parts by the method of the current invention. Then essentially pure HCFC-244bb can be fed into a dehydro-chlorination reactor and a mixture of HCFO-1233xf and other halogenated olefins can be available for further separation known in the art to recover essentially pure HCFO-1233xf for recycle back to the fluorination reactor as described in U.S. Patent Pub. No. 2009-0240090.

Of particular interest is the existence a binary azeotrope or azeotrope-like composition of HCFC-244bb and HCFC-1233xf which is formed as disclosed in U.S. Pat. No. 7,803,283. This binary azeotrope or azeotrope-like composition is then available for separation into its component parts by the method of the current invention. The essentially pure HCFC-244bb can be fed into a dehydrochlorination reactor and essentially pure HCFO-1233xf can be recycled to the fluorination reactor as described in U.S. Patent Pub. No. 2009-0240090.

After a mixture of HCFC-244bb and HCFC-1233xf is separated from impurities, the said mixture in a liquid or gaseous form can be contacted with solid adsorbent such as activated carbon that preferentially adsorbs HCFO-1233xf and then essentially pure HCFC-244bb can be recovered. Relatively pure HCFO-1233xf that is adsorbed by the solid adsorbent can be recovered by means known in the art such as degassing.

In one embodiment, the mixture of HCFC-244bb and HCFO-1233xf is charged into a vessel containing activated carbon maintained at temperature and pressure that are sufficient to keep the mixture liquefied. Then essentially HCFC-244bb is removed from the vessel by filtration. After heating the vessel under vacuum or in the inert gas flow the essentially pure HCFO-1233xf can be recovered from the activated carbon.

In another embodiment, the liquefied mixture of HCFC-244bb and HCFO-1233xf is continuously fed to a column packed with activated carbon. HCFO-1233xf is adsorbed by the activated carbon and essentially pure HCFC-244bb is then collected.

In third embodiment, the mixture of HCFC-244bb and HCFO-1233xf is continuously fed as a vapor to the column packed with activated carbon. HCFO-1233xf is adsorbed on the surface of the activated carbon and essentially pure HCFC-244bb collected.

In fourth embodiment, the mixture of HCFC-244bb and HCFO-1233xf is continuously fed as a vapor to the column packed with activated carbon. HCFO-1233xf is adsorbed on the surface of the activated carbon and essentially pure HCFC-244bb is continuously fed into a vapor phase dehydrochlorination reactor where it is at least partially converted to HFO-1234yf. After separating unreacted HCFC-244bb exiting dehydrochlorination reactor from the HFO-1234yf product and by-products such as HCl and possibly HF, the HCFC-244bb is recycled back into the dehydrochlorination reactor via the purifying column filled with solid adsorbent.

EXAMPLE 1

This example illustrates the removal of halogenated olefins from HCFC-244bb using activated carbon as the solid adsorbent.

120 grams of 99.3 GC area % HCFC-244bb that contained 3350 ppm HCFO-1233xf and 3000 ppm of isomer of HCFO-1224 was added to a 300 cc cylinder that contained 50 cc of Calgon PCB-LS, 4×10 mesh granular activated carbon from the Calgon Carbon Corporation of Pittsburgh, Pa. This activated carbon is a coconut shell based material having a minimum iodine number of 1200.

After shaking and allowing sitting in direct contact with the activated carbon for 1 hour a sample of the liquid was taken and analyzed using the GC used for the original 120 gram sample. GC results showed that the amount of HCFO-1233xf was reduced to 660 ppm and the HCFO-1224 isomer was reduced to 490 ppm. The overall purity of 244bb was increased to 99.8 GC area %. These data show that Calgon PCB-LS activated carbon can selectively remove olefin impurities from HCFC-244bb.

EXAMPLE 2

This example demonstrates the separation of HCFC-244bb from HCFO-1233xf using a solid adsorbent.

50 grams of activated carbon (Calgon PCB-LS, 4×10 mesh) were dried under vacuum at 150° C. for 3 hours. Then 15 grams of activated carbon were charged into 0.5-inch OD PFA (Per Fluor Alkoxy) tube equipped with the valves at the both ends.

A mixture containing 93.55 GC area % 244bb/5.39 GC area % 1233xf was slowly passed as a vapor through a PFA tube filled with 15 grams of Calgon PCB-LS activated carbon to fill a gas sample bag. The contents of a gas bag were analyzed using GC. The Experiment was stopped after concentration of 1233xf in the gas bag sample reached 4.8 GC area %. See Table 1 below.

TABLE 1

| Sample weight (g) | 1233xf Concentration (GC area %) | 244bb Concentration (GC area %) | Total Sample Collected (g) |
|---|---|---|---|
| 4.8 | 1.48 | 97.78 | 4.8 |
| 3.9 | 0.70 | 98.66 | 8.7 |
| 4.8 | 1.68 | 97.75 | 13.5 |
| 3.5 | 2.00 | 97.45 | 17.0 |
| 4.8 | 3.47 | 95.82 | 21.8 |
| 4.7 | 3.84 | 95.45 | 26.5 |
| 4.8 | 4.50 | 94.77 | 31.3 |
| 4.6 | 4.64 | 94.62 | 35.9 |
| 4.2 | 4.81 | 94.46 | 40.1 |

Total weight of material passed through the activated carbon trap was 57.9 g (40.1 g was collected in the gas bags and 17.8 g was adsorbed on carbon). With the assumption that GC area percents (area %) are equal to weight percents, the composition of organic adsorbed on the carbon was 244bb:1233xf=87.83:12.17 (composition of the original mixture 244bb:1233xf=93.55:5.39). The ratio of the weight of adsorbed organics to the weight of activated carbon was 1.19:1.

EXAMPLE 3

This example is similar to Example 1 except Calgon OVC Plus activated carbon was used. This material was obtained from the Calgon Carbon Corporation of Pittsburgh, Pa. This granular activated carbon is a coconut shell based material having a minimum iodine number of 1200.

50 grams of activated carbon (Calgon OVC Plus, 4×10 mesh) were dried under vacuum at 150° C. for 3 hours. Then 14.0 grams activated carbon was charged into 0.5-inch OD PFA tube equipped with the valves at the both ends.

A mixture containing 93.55% 244bb/5.39% 1233xf was slowly passed as a vapor trough a PFA tube filled with 14.0 grams of Calgon OVC plus activated carbon to fill a gas sample bag. The contents of a gas bag were analyzed using GC. This Experiment was stopped after the concentration of 1233xf in the gas bag sample reached 4.8%. The results are shown below in Table 2.

TABLE 2

| Sample weight (g) | 1233xf Concentration (%) | 244bb Concentration (%) | Total Sample Collected (g) |
|---|---|---|---|
| 4.6 | 2.3861 | 96.2026 | 4.6 |
| 6.0 | 1.6227 | 97.4363 | 10.6 |
| 5.8 | 2.9659 | 96.0285 | 16.4 |
| 6.2 | 3.4062 | 95.7592 | 22.6 |
| 4.8 | 4.3169 | 94.8435 | 27.4 |
| 5.7 | 5.0285 | 94.0445 | 33.1 |

Total weight of material passed through the activated carbon trap was 51.19 g (33.1 g was collected in the gas bags and 18.0 g was adsorbed on carbon). With the assumption that GC area percents (area %) are equal to weight percents, the composition of organic adsorbed on the carbon was 244bb:1233xf=90.61:9.391 (composition of the original mixture 244bb:1233xf=93.55:5.39). The ratio of the weight of adsorbed organics to the weight of activated carbon was 1.29:1.

EXAMPLE 4

This is a comparative example. Here, 50 grams of molecular sieve 4 Å were dried under vacuum at 150° C. for 3 hours. Then 9.8 g were charged into 0.5-inch OD PFA tube equipped with the valves at the both ends.

A mixture containing 93.55% 244bb/5.39% 1233xf was slowly passed as a vapor trough a PFA tube filled with 9.8 grams molecular sieve 4 Å pellets to fill a gas sample bag. The contents of a gas bag were analyzed using GC. The concentration of HCFO-1233xf in the first gas bag (about 5 grams collected) was nearly identical to that of in the starting mixture.

This result was a surprise, as molecular sieves and zeolites are known in the art as typically being useful for the adsorption of unsaturated compounds. However, in this instance they did not work, which shows the unexpected advantage of using activated carbon for removing unsaturated compounds from 244bb.

Having thus described a few particular embodiments of the invention, it will be apparent to those skilled in the art, in view of the teachings contained herein, that various alterations, modifications, and improvements not specifically described are available and within the scope of the present invention. Such alterations, modifications, and improvements, as are made obvious by this disclosure, are intended to be part of this description though not expressly stated herein, and are intended to be within the spirit and scope of the invention. Accordingly, the foregoing description is by way of example only, and is not limiting. The invention is limited only as defined in the following claims and equivalents thereto. Finally, all citations made herein to patents, published patent applications and/or literature citations are hereby incorporated herein by reference in their entirety.

What is claimed is:

1. A method for separating the component parts of a binary azeotrope consisting of 2 chloro-1,1,1,2-tetra-fluoropropane (HCFC-244bb) and 2-chloro-3,3,3-trifluoro-propene (HCFO-1233xf) using a solid adsorbent that adsorbs the HCFO-1233xf, whereby the HCFC-244bb is separated therefrom and wherein the solid adsorbent comprises activated carbon having a minimum iodine number within the range of 900 to 1200.

2. The method of claim 1, wherein the activated carbon has a minimum Iodine Number of 900.

3. The method of claim 1, wherein the activated carbon has a minimum Iodine Number of 1000.

4. The method of claim 1, wherein the activated carbon has a minimum Iodine Number of 1100.

5. The method of claim 1, wherein the activated carbon has a minimum Iodine Number of 1200.

6. The method of claim 1, wherein the activated carbon is a coconut shell based carbon.

7. The method of claim 1, wherein the activated carbon is a coal based carbon.

8. The method of claim 1, wherein the mixture is passed over the solid adsorbent for a period of time sufficient to adsorb the HCFO-1233xf.

9. The method of claim 4, wherein the solid adsorbent is regenerated after use to remove the HCFO-1233xf adsorbed thereon.

10. The method of claim 1, wherein the solid adsorbent is added to the mixture for a period of time sufficient to adsorb the HCFO-1233xf.

11. The method of claim 10, wherein the solid adsorbent is regenerated after use to remove the HCFO-1233xf adsorbed thereon.

12. A method of separating a mixture of HCFC-244bb and HCFC-1233xf comprising passing the mixture in a liquid or gaseous form through an activated carbon solid adsorbent having a minimum iodine number within the range of 900 to 1200, whereby the activated carbon adsorbs the HCFO-1233xf and then essentially pure HCFC-244bb can be recovered.

13. The method of claim 12, wherein the HCFO-1233xf that is adsorbed by the activated carbon is recovered by degassing.

* * * * *